United States Patent [19]

Martens et al.

[11] Patent Number: 5,376,332
[45] Date of Patent: Dec. 27, 1994

[54] PLASMA STERILIZING WITH DOWNSTREAM OXYGEN ADDITION

[75] Inventors: Phillip A. Martens, Fremont; Bryant A. Campbell, Los Gatos, both of Calif.

[73] Assignee: ABTOX, Inc., Mundelein, Ill.

[21] Appl. No.: 20,904

[22] Filed: Feb. 22, 1993

Related U.S. Application Data

[63] Continuation of Ser. No. 652,329, Feb. 6, 1991, abandoned.

[51] Int. Cl.⁵ .............................................. A61L 2/00
[52] U.S. Cl. ...................................... 422/23; 422/22; 422/28; 422/33
[58] Field of Search .................. 422/23, 28, 33, 32, 422/123, 906, 22

[56] References Cited

U.S. PATENT DOCUMENTS

| | | | |
|---|---|---|---|
| 3,383,163 | 5/1968 | Menashi | 422/23 |
| 3,410,776 | 11/1968 | Bersin . | |
| 3,428,548 | 2/1969 | Hollahan . | |
| 3,704,096 | 11/1972 | Verses et al. . | |
| 3,737,608 | 6/1973 | Nagao et al. . | |
| 3,851,436 | 12/1974 | Fraser et al. . | |
| 3,948,601 | 4/1976 | Fraser et al. | 422/23 |
| 4,065,369 | 12/1977 | Ogawa et al. . | |
| 4,123,663 | 10/1978 | Horiike . | |
| 4,138,306 | 2/1979 | Niwa . | |
| 4,151,034 | 4/1979 | Yamamoto . | |
| 4,160,690 | 7/1979 | Shibagaki . | |
| 4,169,123 | 9/1979 | Moore et al. . | |
| 4,169,124 | 9/1979 | Forstrom et al. . | |
| 4,207,286 | 6/1980 | Boucher . | |
| 4,230,663 | 10/1980 | Forstrom et al. . | |
| 4,289,728 | 9/1981 | Peel et al. . | |
| 4,321,232 | 3/1982 | Bithell | 422/23 |
| 4,348,357 | 9/1982 | Bithell . | |
| 4,366,125 | 12/1982 | Kodera et al. . | |
| 4,437,567 | 3/1984 | Jeng . | |
| 4,643,876 | 2/1987 | Jacobs et al. . | |
| 4,801,427 | 1/1989 | Jacob | 422/23 |
| 4,818,488 | 4/1989 | Jacob . | |
| 4,898,715 | 2/1990 | Jacob . | |
| 4,917,586 | 4/1990 | Jacob . | |
| 4,931,261 | 6/1990 | Jacob . | |
| 4,943,417 | 6/1990 | Jacob . | |
| 4,976,920 | 12/1990 | Jacob . | |

FOREIGN PATENT DOCUMENTS

| | | |
|---|---|---|
| 087825 | 5/1983 | Japan . |
| 103460 | 6/1983 | Japan . |
| 162276 | 9/1983 | Japan . |

OTHER PUBLICATIONS

A. Russell (Ed.), *The Destruction of Bacterial Spores*, New York: Academic Press (1982).

Fraser et al., "Plasma Sterilization Technology for Spacecraft Applications," NASA-CR-146314 Final Report (Boeing Co.), Sep. 1975.

Hallohan et al., "Analytical Applications of Electrodelessly Discharged Gases" Chemical Instrumental, J. of Chem. Education, 43:A401–416, May 1966.

Hallohan et al., "Research with Electrodelessly Discharged Gases," Chem. Instrument, 43:A497–A512, Jun. 1966.

Hallohan et al., "Chem. Education Letters," J. of Chem. Educ. 43:392–393 Jul. 1966.

Hallohan et al. "Techniques and Application of Plasma Chem.," v–vii, 229–253, 1974.

Rudder et al., "Remote Plasma-Enhanced Chemical-Vapor Deposition of Epitaxial Ge Films," J. of Appl. Phys., 60(1):352, Nov. 15, 1986.

*Primary Examiner*—Robert J. Warden
*Assistant Examiner*—Krisanne M. Thornton
*Attorney, Agent, or Firm*—Majestic, Parsons, Siebert & Hsue

[57] ABSTRACT

A method for plasma sterilization includes forming a gas plasma from a substantially oxygen-free mixture containing argon or helium and from 1% to 5% (v/v) hydrogen in a plasma generating chamber, and exposing an article to be sterilized in a sterilizing chamber to a non-explosive mixture of the plasma gas and from 1% up to 20% (v/v) oxygen gas. Preferably, the pressure in the sterilizing chamber is from 0.1 to 10 torr and the chamber temperature is less than 6° C., the mixture from which the plasma is generated contains from 4% to 5% (v/v) hydrogen, and the article in the sterilizing chamber is exposed to a mixture of plasma gas and from 1% to 10% (v/v) oxygen.

11 Claims, 9 Drawing Sheets

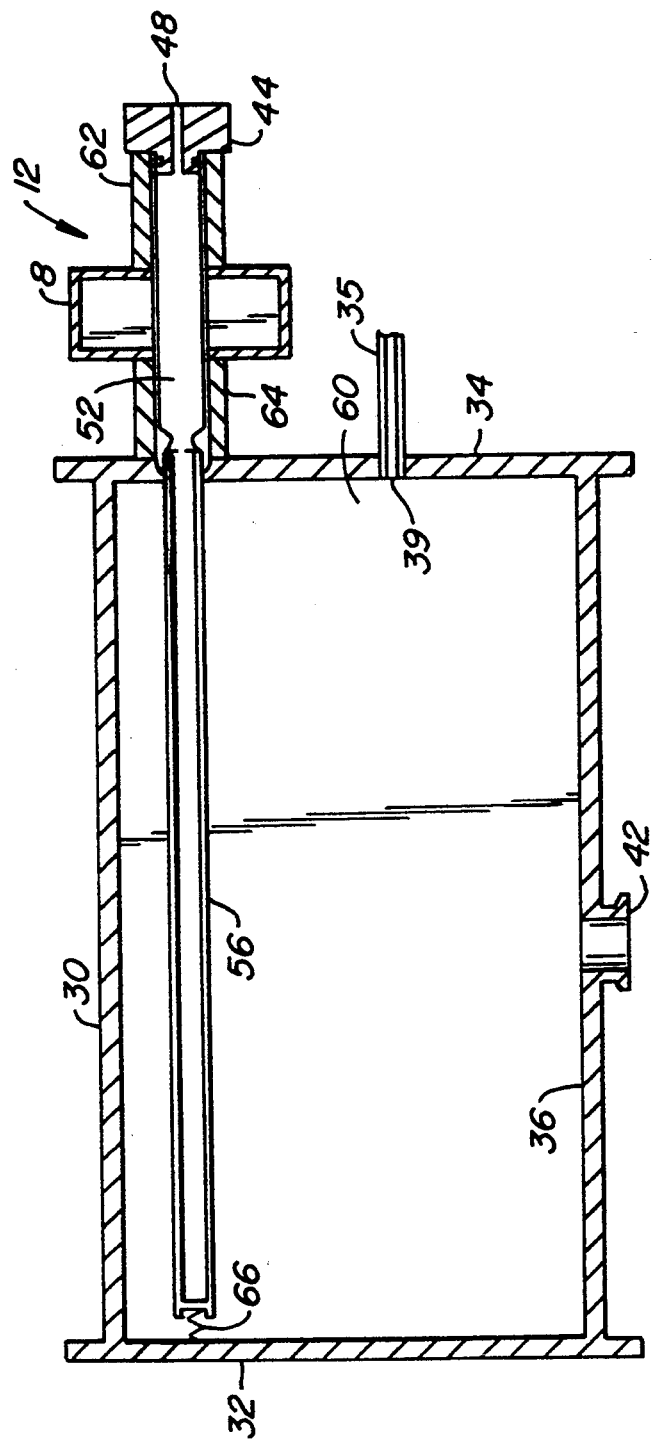
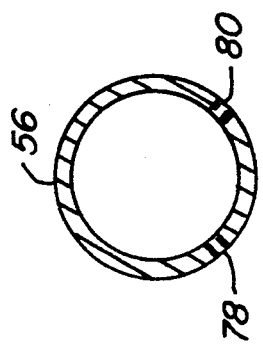
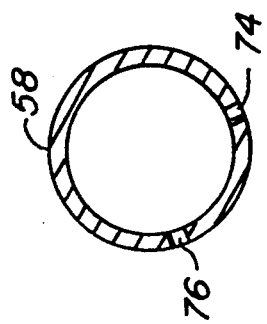
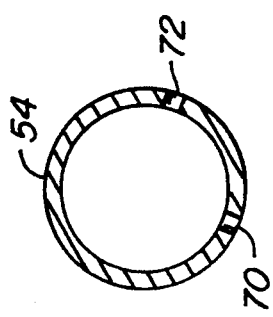
FIG. 4.
FIG. 5.
FIG. 6.
FIG. 7.

PLASMA STERILIZING WITH DOWNSTREAM OXYGEN ADDITION

This is a continuation of application Ser. No. 652,329, filed Feb. 6,1991, now abandoned.

COPENDING APPLICATIONS

Applications Ser. No. 07/576,292 filed Aug. 31, 1990 now U.S. Pat. No. 5,115,166, Ser. No. 07/475,602 filed Feb. 6, 1990 now abandoned and Ser. No. 07/321,483 filed Mar. 8, 1989 now abandoned by Bryant A. Campbell and Kern A. Moulton entitled PLASMA STERILIZER AND METHOD.

Applications Ser. No. 07/576,231 filed Aug. 31, 1990 now abandoned and Ser. No. 07/522,271 filed May 11, 1990 now abandoned by Bryant A. Campbell, Kern A. Moulton, and Ross A. Caputo entitled STERILIZING WITH PERACID AND PLASMA.

Applications Ser. No. 07/576,236 filed Aug. 31, 1990 now abandoned and Ser. No. 07/522,421 filed May 11, 1990 now abandoned by Bryant A. Campbell, Kern A. Moulton, and Ross A. Caputo entitled STERILIZING WITH HYDROGEN PEROXIDE AND PLASMA.

Application Ser. No. 07/576,235 filed Aug. 31, 1990 now U.S. Pat. No. 5,084,239 by K. A. Moulton, R. A. Caputo and B. A. Campbell entitled PLASMA-STERILIZING PROCESS WITH PULSED ANTI-MICROBIAL AGENT TREATMENT.

Application Ser. No. 07/576,294 filed Aug. 31, 1990 now U.S. Pat. No. 5,186,893 by Kern A. Moulton, Bryant A. Campbell, and Ross A. Caputo entitled PLASMA CYCLING STERILIZING PROCESS.

Application Ser. No. 07/589,511 filed Sep. 28, 1990 now U.S. Pat. No. 5,184,046 by Bryant A. Campbell entitled CIRCULAR WAVEGUIDE PLASMA MICROWAVE STERILIZER APPARATUS.

Application Ser. No. 07/576,325 filed Aug. 31, 1990 now U.S. Pat. No. 5,178,829 by K. A. Moulton, R. A. Caputo and B. A. Campbell entitled FLASH STERILIZATION WITH PLASMA.

FIELD OF THE INVENTION

This invention relates to a process for sterilizing articles with gas plasmas. In particular, this invention relates to an improved method for sterilizing articles with a plasma derived gas generated from a mixture of one or more inert gases such as argon or helium, and hydrogen gases with addition of oxygen downstream from the plasma generating chamber.

BACKGROUND OF THE INVENTION

A variety of gas sterilization methods have been investigated in the past. Methods using ethylene oxide and other disinfecting gases are used for sterilizing a wide range of medical products ranging from pharmaceutical preparations to surgical instruments. Irradiation alone or together with disinfecting gases has also been investigated, as summarized by Russell, A. THE DESTRUCTION OF BACTERIAL SPORES. New York: Academic Press (1982) .

A sterilizing method must effectively kill all organisms, including spores, without damage to the article or goods being sterilized. However, irradiation methods and disinfecting gases such as ethylene oxide, which meet this criteria, are now recognized to expose workers and the environment to safety hazards. State and Federal legislation are severely restricting the amount of hazardous gases such as ethylene oxide (a carcinogen) in the working environment and the use of any system or method which produces toxic residues or exhaust products. This is causing a major crisis in hospitals and in other areas of the health industry.

DESCRIPTION OF THE PRIOR ART

The use of plasma to sterilize containers was suggested in U.S. Pat. No. 3,383,163. Plasma is partially ionized gas which may be generated by the application of an electromagnetic field. The ionized gas will contact microorganisms on the surfaces of the items to be sterilized and effectively destroy the microorganisms.

Sterilizing plasmas have been generated with a wide variety of gases: argon, helium or xenon (U.S. Pat. No. 851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or freon with pulsed pressure (U.S. Pat. No. 4,348,357); hydrogen peroxide (U.S. Pat. 4,643,876); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasmas have proven to be too corrosive to articles being sterilized, in particular cellulosic packaging materials; have left toxic residues on the sterilized articles; or have presented safety or environmental hazards.

Non-plasma gas sterilization procedures have been described using ozone (U.S. Pat. No. 3,704,096) and hydrogen peroxide (U.S. Pat. Nos. 4,169,123, 4,169,124, 4,230,663, 4,366,125, 4,289,728, 4,437,567 and 4,643,876). These materials are toxic and leave undesirable residues.

The plasma gas sterilizer systems described in U.S. Pat. Nos. 3,851,436 and 3,948,601 have a RF plasma generation chamber and a separate sterilizing chamber. Gas plasma is produced in the plasma chamber from argon, helium, nitrogen, oxygen or xenon, and the gas plasma product is passed into a separate sterilization vacuum chamber. U.S. Pat. No. 4,643,876 describes a hydrogen peroxide plasma RF generation chamber which also functions as the sterilizing chamber. Matching networks are required with the RF systems to adjust to the conductivity variations in the plasma generating zone produced by the articles being sterilized.

OBJECTS AND SUMMARY OF THE INVENTION

It is an object of this invention to provide an improved plasma sterilizing process which carries out effective sterilization, quickly, with no toxic residues and with emissions which present no environmental safety hazard and without damage to non-metallic articles and packaging materials.

It is another object of this invention to provide an economical sterilizing process which is safe and effective for use in a hospital environment.

It is a further object of this invention to provide effective sterilization at a selected maximum temperature, with rapid sterilization kinetics (or effective sterilizing rate), and with non-explosive gas mixtures containing hydrogen.

The method of this invention for plasma sterilization comprises forming a gas plasma from a substantially oxygen-free mixture containing argon or helium and from 1% to 5% (v/v) hydrogen in a plasma generating chamber, and exposing an article to be sterilized in a sterilizing chamber to the mixture of the plasma gas and from 1% up to 20% (v/v) oxygen gas.

Preferably, the pressure in the sterilizing chamber is from 0.1 to 10 torr and the chamber temperature is less than 60° C., the mixture from which the plasma is generated contains from 4% to 5% (v/v) hydrogen, and the article in the sterilizing chamber is exposed to a mixture of plasma gas and from 15% to 20% (v/v) oxygen.

BRIEF DESCRIPTION OF THE DRAWINGS

FIG. 4 is a cross-sectional view of the plasma sterilizer embodiment of FIG. 3, taken along the line 4—4.

FIG. 5 is a cross-sectional view of tube 54 taken along line 5—5 in FIG. 3.

FIG. 6 is a cross-sectional view of tube 58 taken along line 6—6 in FIG. 3.

FIG. 7 is a cross-sectional view of tube 56 taken along line 7—7 in FIG. 3.

DETAILED DESCRIPTION OF THE INVENTION

Figure 1:
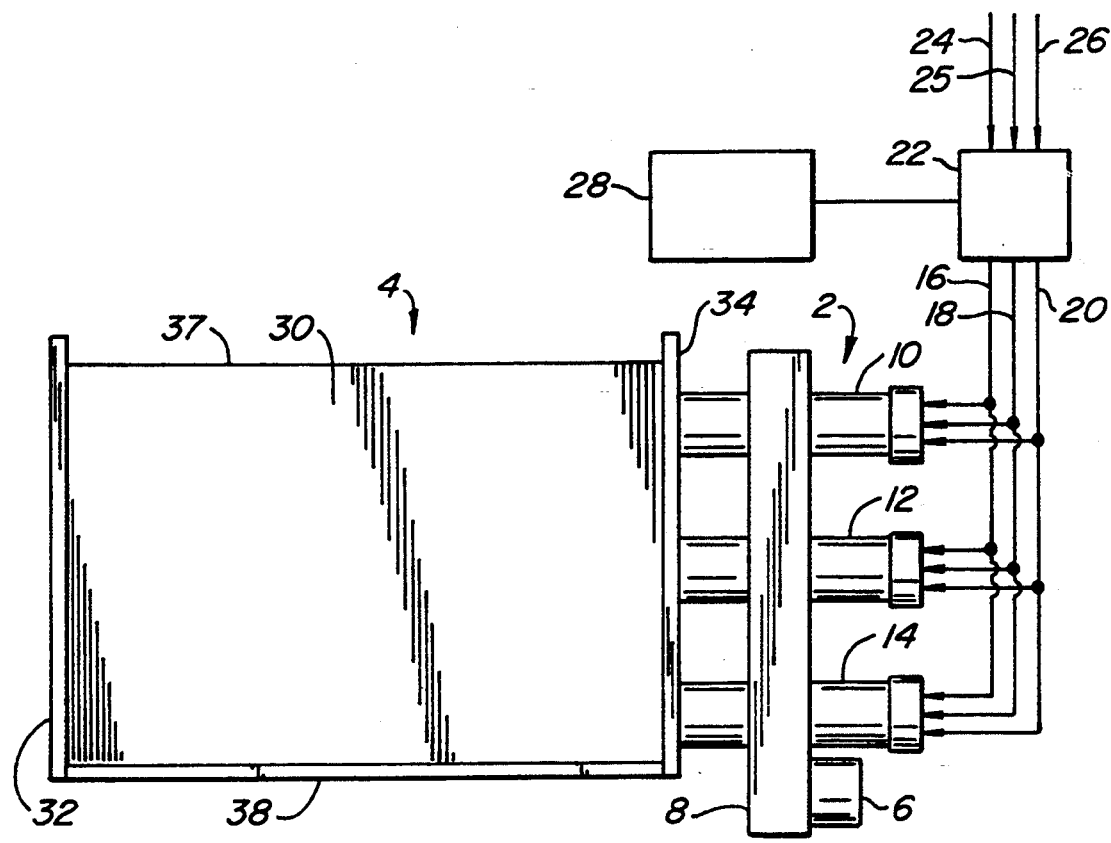
FIG. 1 is a top view of a plasma sterilizer suitable for use in the process of this invention.

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. However, ethylene oxide is now known to be a dangerous carcinogen, and a number of new state laws protecting worker safety and the environment are precluding further use of ethylene oxide sterilizers in hospital environments.

Numerous gas plasma sterilizers using a wide variety of gases have been described in the patent literature. Several have been commercially produced. A few have focused on residue contamination problems. The previously described gas sterilizers fail to satisfy current regulatory residue and exhaust emission safety standards of several states because they either leave unacceptable residues, produce exhaust emissions which are potentially hazardous to hospital personnel, or cause unacceptable destruction of packaging materials.

In the process of this invention, the gas sterilizer produces a plasma from gas mixtures containing hydrogen and inert gases such as argon or helium. The plasma gas is mixed with oxygen gas in the sterilizing chamber. The exhaust gas products fully satisfy current environmental and worker safety concerns, the products of the plasma being almost entirely water vapor, carbon dioxide, and other non-toxic gases normally found in the atmosphere.

The term "plasma" as used herein is defined to include any portion of the gas or vapors which contain electrons, ions, free radicals, dissociated and/or excited atoms or molecules produced as a result of an applied electric or electromagnetic field including any accompanying radiation which might be produced. The electromagnetic field can cover a broad frequency range, and can be produced by a magnetron, klystron or RF resonant circuit. For purposes of clarity of presentation and not by way of limitation, the description hereinafter describes the use of a magnetron as the electromagnetic field source, and the use of all other suitable sources of the electromagnetic field required for plasma production are intended to be included, including without limitation, magnetrons, klystron tubes, RF resonant circuits, and the like.

The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability of organism survival (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-6}$ would become $10^{-12}$.

The sterilizing rate with plasma gases is temperature dependent, the rate increasing with increasing temperature. However, the corrosive properties of the plasma gases also increase with temperature. Sterile articles are often maintained in a sterile condition by enclosing them in packages including porous organic layers. These packages have cellulosic panels through which sterilizing gases diffuse to sterilize the package contents. The cellulosic layers are particularly vulnerable to oxidation in the presence of plasma gases generated from gas mixtures containing oxygen. As the cellulosic layers deteriorate, they allow the entrance of microorganisms into the package, and the packaging becomes ineffective to maintain sterility.

Plasma generated from mixtures of hydrogen and inert gases is far less damaging to cellulosic packaging materials; however, such a plasma has little sterilizing effect. Cellulose is relatively resistant to unactivated oxygen gases. However, molecular oxygen has little if any sterilizing effect.

We have discovered that when oxygen gas is mixed with plasma gases produced from a mixture of hydrogen and an inert gas such as argon or helium, a highly effective sterilizing mixture is formed. Furthermore, sterilization can be achieved with this mixture at low temperatures without significant damage to cellulosic packaging materials.

For sterilizing packaged articles, an article in a sterilizing chamber is exposed to a gas plasma generated in a plasma generating chamber from a mixture of gases consisting essentially of argon, helium, or mixtures thereof; and from 1 to up to a maximum of 20% (v/v) hydrogen, and preferably from 1% to 5% (v/v) hydrogen. Higher concentrations of hydrogen can be used, insofar as sterilizing process efficiency is concerned. However, because hydrogen concentrations in hydrogen/oxygen mixtures above a certain level are explosive, the upper practical limit of the hydrogen concentration is the upper amount which will not form an explosive mixture with oxygen in the sterilizing chamber.

Oxygen gas alone or mixed with an inert gas such as neon, argon or mixtures thereof is mixed with the gas plasma product downstream of the plasma generating chamber. The amount of oxygen is also selected to avoid forming an explosive mixture. The oxygen is preferably introduced in the form of a mixture of up to 20% (v/v) oxygen, the remainder of the gas (80% and above) being an inert gas. The final concentration of oxygen in the sterilizing chamber is preferably from 1% to 10% (v/v).

The exposure to the plasma gases is preferably carried out at a pressure of from 0.1 to 10 torr and preferably from 1 to 10 torr. A preferred maximum preselected temperature in the sterilizing chamber is about 60° C. Higher temperatures can be used, provided there is no significant damage to the packaging materials at the elevated temperatures in the time required to effect sterilization.

For articles including organic polymers which are sensitive to plasma gases, a preselected maximum temperature is about 60° C. For metal articles such as stainless steel articles, the maximum preselected temperature can be a much higher temperature. A maximum preselected temperature for metal articles is conveniently about 80° C.

The method of this invention for plasma sterilization comprises exposing an article to be sterilized to a mixture of oxygen and a plasma generated from a gaseous mixture of hydrogen and an inert gas such as argon, helium or mixtures thereof at the preselected maximum temperature, a pressure of from 0.1 to 10 torr, and a treatment time of at least 5, and preferably from 10 to 15 minutes.

The plasma sterilizers suitable for use in the process of this invention have a plasma generator chamber separate from the sterilizing chamber, and the gas plasma products flow from the plasma generating chamber into the sterilizing chamber containing an article to be sterilized.

In an optimum method of sterilizing, the articles to be sterilized are placed in the sterilizing chamber, supported by conventional grids which permit the plasma to reach all surfaces of the articles. The chamber is closed, the sterilizing chamber is evacuated, and plasma feed gas flow into the plasma generator and oxygen gas flow into the sterilizing chamber is initiated. The electromagnetic field is initiated, plasma generation is begun in a plasma generating chamber, and the plasma gas products flow into and through the sterilizing chamber. Oxygen gas (molecular oxygen) mixes with the plasma gas products in the sterilizing chamber.

The plasma components have a short life, and quickly decay to form water vapor (gas), carbon dioxide, and other non-toxic components usually found in air. These are fully acceptable as exhaust gas components.

Figure 2:
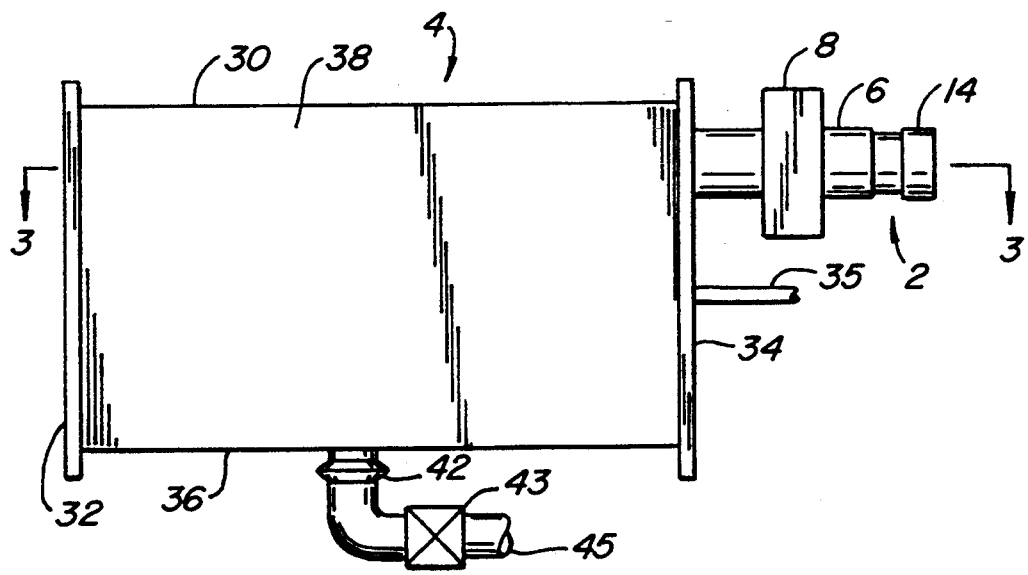
FIG. 2 is a front view of the plasma sterilizer embodiment of FIG. 1.

FIG. 1 is a top view and FIG. 2 is a front view of a single waveguide plasma sterilizer embodiment. The plasma sterilizer has a plasma generator 2 and a sterilizing chamber 4. The plasma generator 2 comprises an electromagnetic field generator such as a magnetron 6 and a waveguide 8 which directs and contains the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are welded or otherwise sealed together to form a vacuum chamber. The door 38 forms a seal with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. An optimum material is pure (98%) aluminum which can be applied either as a liner or as a flame-sprayed coating on all internal walls of the stainless steel chamber. An alternate material is nickel.

Oxygen gas can be introduced through conduit 35 to inlet port 39 (FIG. 4). The gases are exhausted from the sterilizing chamber through exhaust outlet port 42, isolation valve 43, and exhaust conduit 45 to a conventional vacuum pump system (not shown).

Figure 3:
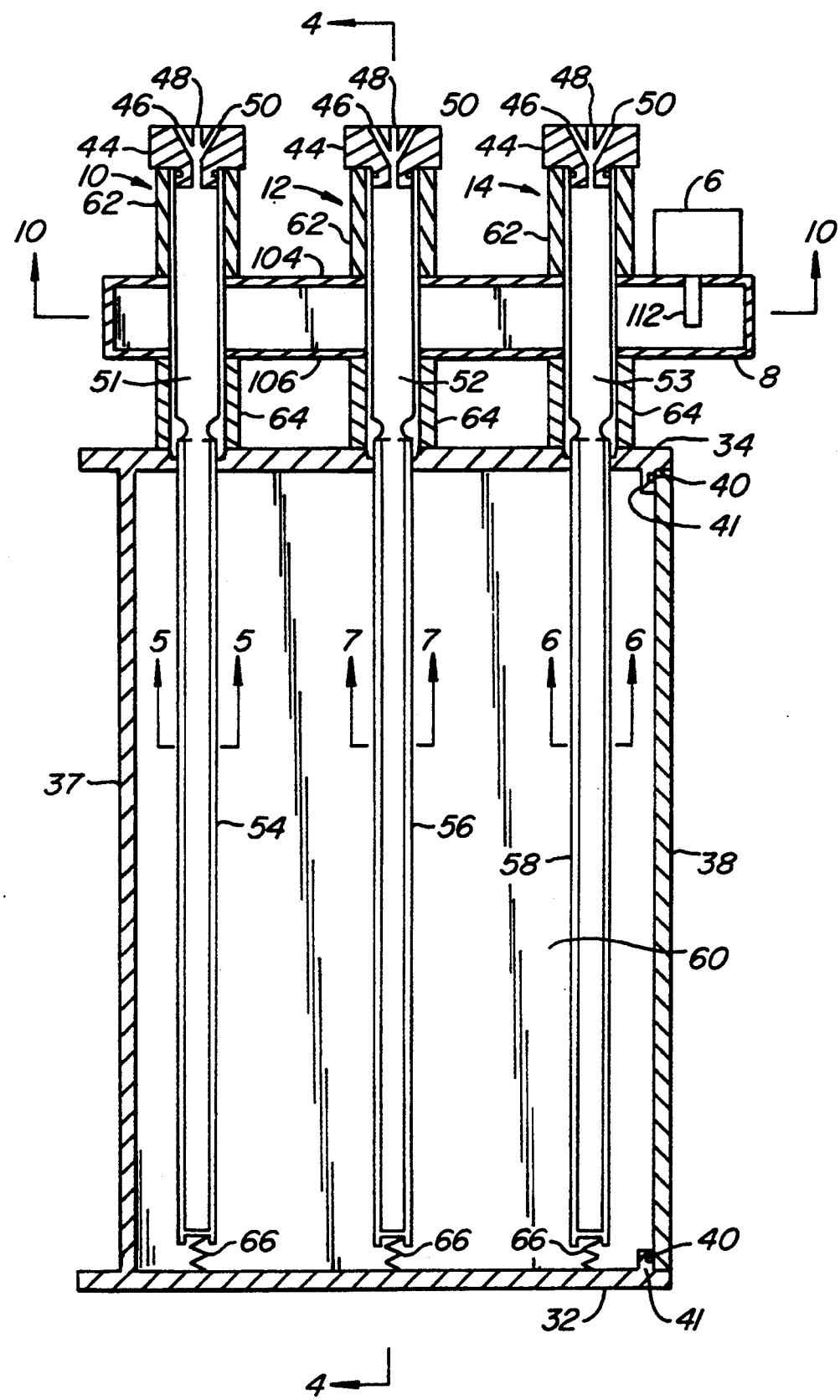
FIG. 3 is a cross-sectional view of the plasma sterilizer embodiment of FIG. 1 and FIG. 2, taken along the line 3—3 in FIG. 2.

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. The gas generator tubes must be transparent to the electromagnetic field. In the waveguide 8, the gases are energized and converted in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with grooves or cooling fins (not shown) in a conventional manner to increase their efficiency in removing heat from gas generator tubes. The distal ends of the gas distribution tubes 54, 56 and 58 are supported by spring-biased end supports 66 mounted on side plate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamp or latch devices can be used to insure closure of the door before chamber evacuation is initiated.

FIG. 5, FIG. 6 and FIG. 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

Figure 8:
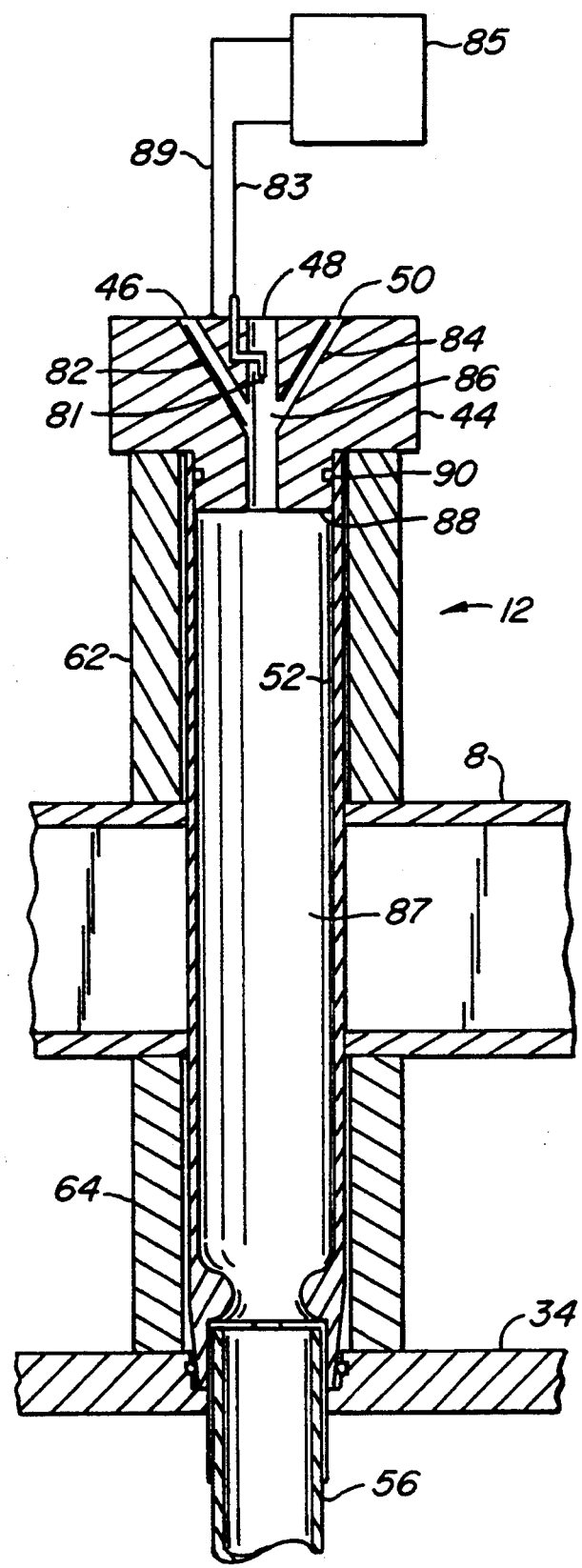
FIG. 8 is a partial cross-sectional view of the plasma generator tube and assembly of the embodiment of FIG. 1.
Figure 9:
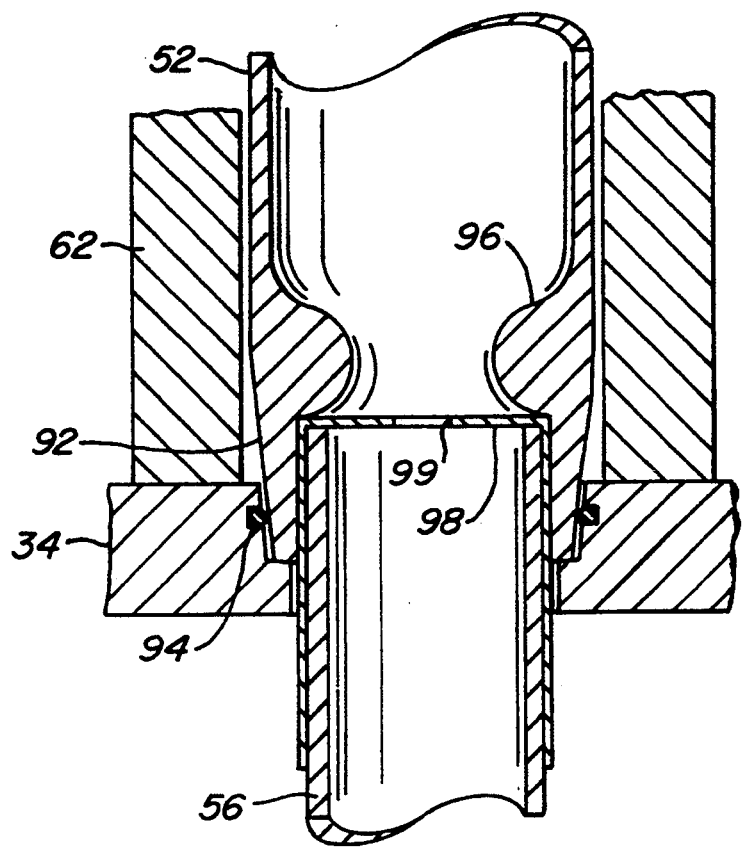
FIG. 9 is a partial, fragmentary, cross-sectional detail view of the plasma generator tube of the plasma generator shown in FIG. 8.

FIG. 8 is a partial top cross-sectional detail fragmentary view of plasma generator tube 12 of FIG. 3, and FIG. 9 is a more detailed view of the plasma generator tube outlet assembly shown in FIG. 3. The gas inlet ports 46 and 50 in the gas inlet cap 44 are connected by passageways 82 and 84 to the gas inlet passageway 86 leading from inlet port 48. The gases fed to the inlet ports are mixed in the passageway 86. The gas mixture passes into the proximal end of the tube 52 and through the excitation zone 87 within the waveguide 8 where the plasma is formed. The proximal end of the plasma generator tube 52 is supported on cylindrical projection 88. O-ring 90 or another type of seal forms a gas-tight seal therewith, thereby maintaining a reduced pressure in the tube 52 and preventing leakage of atmospheric gas into the system.

In this sectional view, an optional plasma starter ionizer is shown. The tip 81 is connected by an insulated conduit 83 (shown schematically) to a power supply 85 which can be powered with a standard 115 V AC power source. A ground conduit 89 from the power supply connects to the gas inlet cap 44. The electric field ionizes a portion of the gas molecules flowing from opening 48 through passageway 86, the ionized gases quickly supporting a plasma as the gases pass through the zone 87. The ionizer can be placed in any of the inlet gas passageways of any of the embodiments of this plasma sterilizer.

Referring to FIG. 9, the outer surface 92 of the distal end of the plasma generator tube 52 is tapered inward and is sealed by O-ring 94 or other form of seal with the backplate 37. The distal end of tube 52 has increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this embodiment, creating a pressure difference between the low pressure plasma generating zone 87 and the vacuum pressure in the distribution tube 56 and sterilizing chamber 60.

The diameter of the restrictive opening 99 is preferably selected to maintain a back pressure of from 0.3 to 10 torr, preferably from 1 to 5 torr and optimally from 5 to 6 torr in the plasma generating zone with a vacuum chamber pressure in the range of from 0.3 to 2 torr. This pressure provides optimum energy consumption and plasma generation. For most operating parameters, the restriction 99 can have a diameter of from 4.82 to 8.00 mm and preferably from 6.28 to 6.54 mm.

Figure 10:
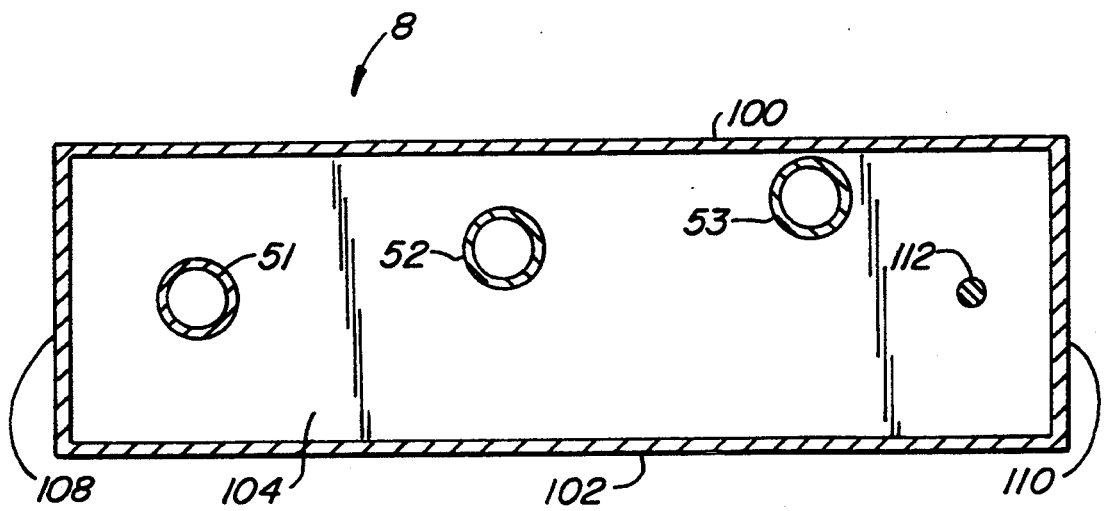
FIG. 10 is a cross-sectional view of the waveguide of the embodiment of FIG. 1, taken along the line 10—10 in FIG. 3.

FIG. 10 is a cross-sectional view of the waveguide of the embodiment of FIG. 1, taken along the line 10—10 in FIG. 3. The waveguide is formed of top and bottom plates 100 and 102, side plates 104 and 106 (FIG. 3), and end plates 108 and 110, welded or bolted together. A single magnetron rod 112 is placed in the end of the waveguide 8. The plasma generating tubes 51, 52 and 53 are positioned in the waveguide 8. The positions of the plasma generating tubes are selected to provide maximum conversion of the electromagnetic field energy to plasma. Tube 53 is positioned in a zone to interact with a third of the field and not with zones of the field which will interact with tubes 51 and 52. Tube 52 is positioned in a zone to interact with a third of the field (half of the remaining field) and not with the field zone which will interact with tube 51. Tube 51 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave.

Three tubes have been shown in FIG. 10 by way of example and not by way of limitation. Any number, odd or even, of tubes can be used up until the total power of the electromagnetic field is absorbed.

Figure 11:
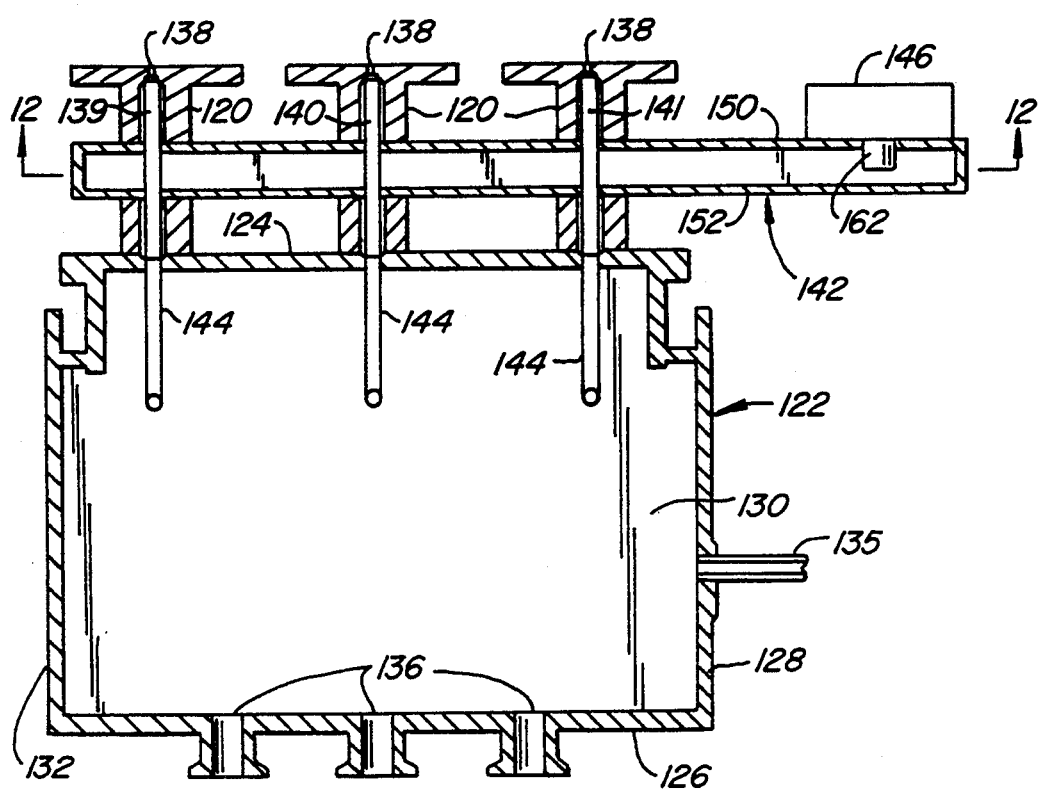
FIG. 11 is a side cross-sectional view of an alternate single waveguide embodiment of the plasma sterilizer suitable for use in the process of this invention.

FIG. 11 is a front cross-sectional view of an alternate single wave guide embodiment of the plasma sterilizer. Three plasma generating units 120 are positioned above the sterilizing chamber 122 defined by upper plate 124, lower plate 126, back plate 128, back plate 130 and side plates 128 and 132. The door plate (not shown) can be mounted to the front of the chamber as described above with respect to FIG. 2 and FIG. 3 and forms a sealed engagement with the front edges of the chamber walls. Oxygen gas can be introduced through conduit 135 (FIG.11). The gases are exhausted from the chamber through exhaust ports 136 in the floor plate 126.

The plasma generators comprise an inlet port for mixed gases 138 leading to the plasma generating tubes 139, 140 and 141 positioned in the waveguide 142 where the gases are energized and converted to a plasma. The plasma is directed by the plasma distributors 144 to the interior of the sterilizing chamber 122. Each plasma distributor 144 can have a T-configuration described below in detail with respect to the embodiment of FIG. 14. The plasma generating source in this embodiment is a magnetron 146 positioned at the end of the waveguide 142.

Figure 12:
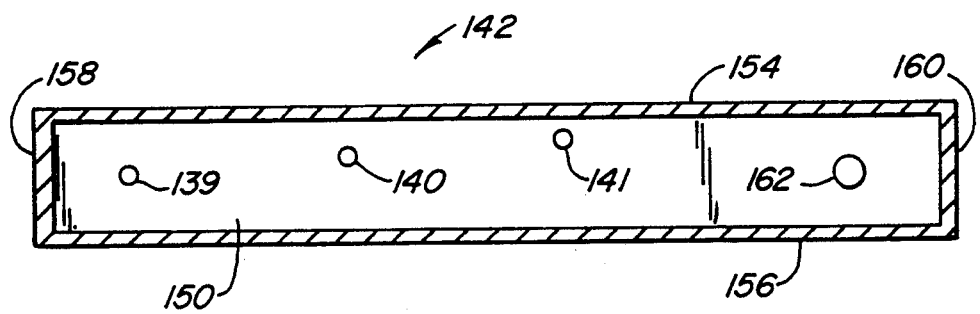
FIG. 12 is a cross-sectional view of the waveguide of the embodiment of FIG. 11, taken along the line 12—12.

FIG. 12 is a cross-sectional view of the waveguide of embodiment of FIG. 11, taken along line 12—12 in FIG. 11. The waveguide is formed of top and bottom plates 150 and 152 (FIG. 11), side plates 154 and 156, and end plates 158 and 160, welded or bolted together. A single magnetron rod 162 is placed in the end of the waveguide 142. The plasma generating tubes 139, 140 and 141 are positioned in the waveguide 142. The positions of the plasma generating tubes are selected to provide maximum conversion of the electromagnetic field energy to plasma. Tube 141 is positioned in a zone to interact with a third of the field and not with zones of the field which will interact with tubes 140 and 139. Tube 140 is positioned in a zone to interact with a third of the field (half of the remaining field) and not with the field zone which will interact with tube 139. Tube 139 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave. Three tubes have been shown in FIG. 12 by way of example and not by way of limitation. Any number, odd or even, of tubes can be used up until the total power of the electromagnetic field is absorbed.

The detailed construction of the plasma generator tube and plasma distribution tube seals and flow restrictors has the same configuration as the corresponding elements in the embodiment of FIG. 11 and is described in greater detail hereinabove in conjunction therewith.

Figure 13:
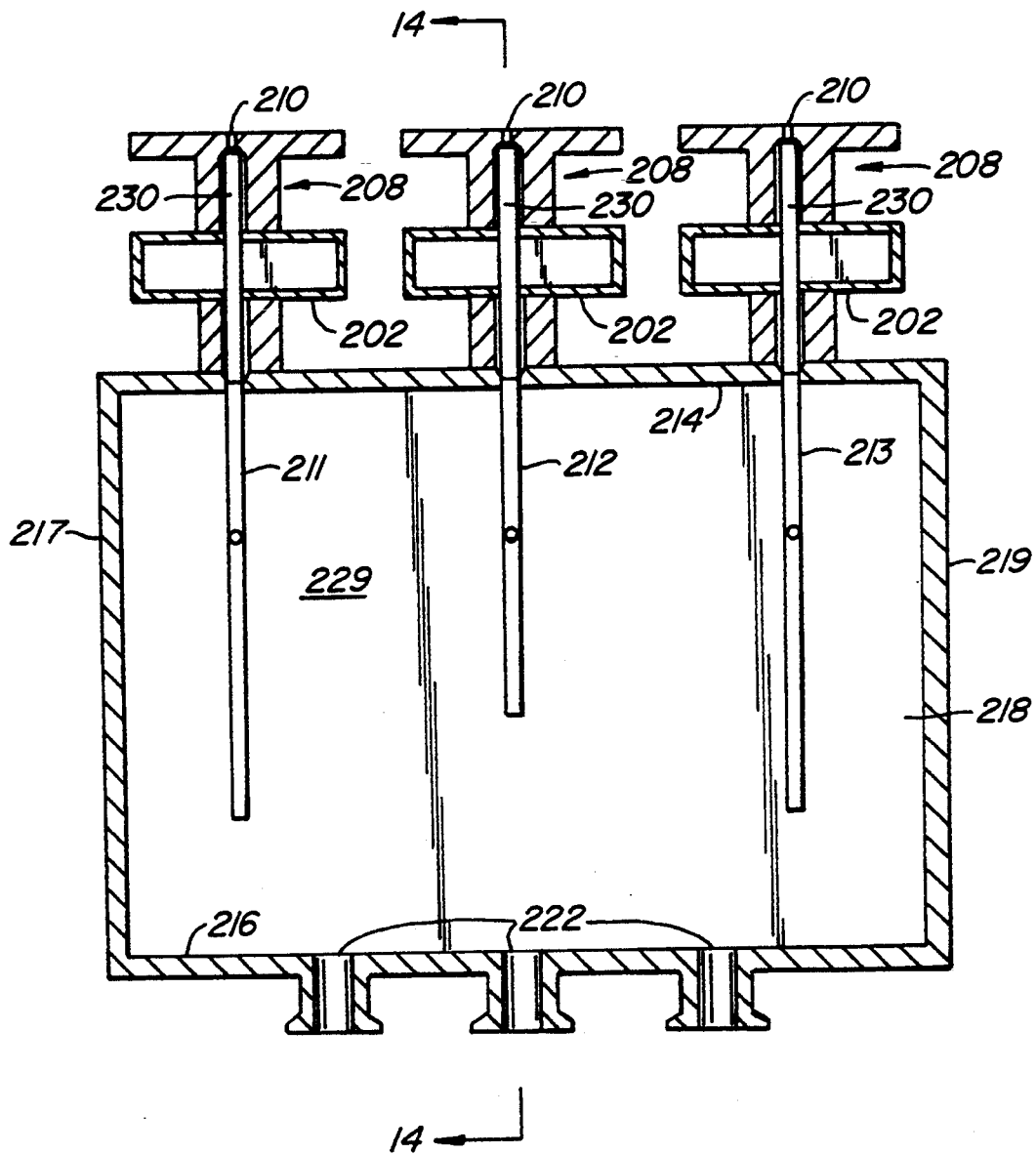
FIG. 13 is a side cross-sectional view of a multiple magnetron embodiment.
Figure 14:
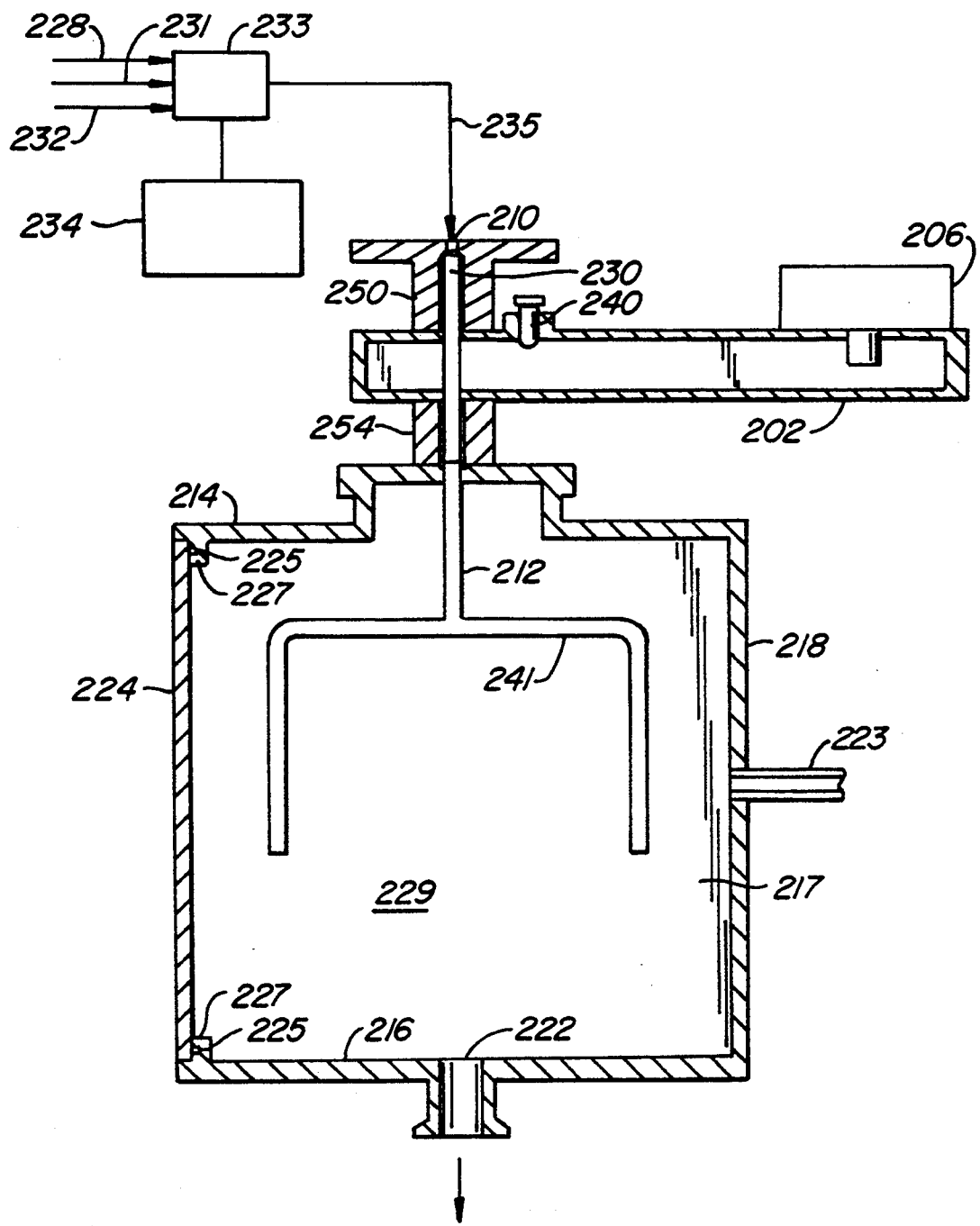
FIG. 14 is a front cross-sectional view of the multiple waveguide embodiment of the plasma sterilizer, taken along the line 14—14 of FIG. 13.

FIG. 13 is a front cross-sectional view of a multiple magnetron plasma sterilizer embodiment, and FIG. 14 is a side cross-sectional view taken along the line 14—14 in FIG. 13. Three plasma generators 208 of this embodiment are positioned above the sterilizing chamber cavity 229, each producing a plasma generated from a gas mixture introduced through inlets 210 to a plasma generating tube 230 positioned in the respective waveguides 202. The plasma produced is fed by plasma generating tubes 230 through respective gas distributors 211, 212 and 213 into the sterilizing chamber 229.

The sterilizing chamber 229 is constructed from metal plates welded to form a gas-tight construction which is able to withstand external pressures when the chamber is evacuated. The construction comprises top plate 214, bottom plate 216, back plate 218, side plates 217 and 219. Exhaust ports 222 are mounted in the bottom plate 216. Oxygen gas can be introduced through conduit 223 (FIG.14). The door 224 is supported by conventional pin hinges or the like (not shown) mounted on the side, top or bottom of the chamber walls as described above with respect to the embodiment of FIG. 1. The door 224 is held in sealing engagement by atmospheric pressure against the O-ring seal 225 mounted in the flange 227 extending from the side plates 217 and 219, and the top and bottom plates 214 and 216 (not shown). Optionally, additional conventional closure clamp or latch devices can be used to insure closure of the door before chamber evacuation is initiated.

Referring to FIG. 14, the inert and hydrogen gases are fed by inlet lines 228, 231 and 232 to the control valve and gas mixing unit 233 controlled by CPU 234. The gas mixture is fed to the inlet port 210 by conduit 235 and then to the plasma generating tube 230 where it is energized to form a gas plasma. The control valves and CPU can be any of the conventional, standard devices used for gas flow control in plasma generating equipment. The waveguide 202 guides the electromagnetic waves generated by the magnetron 206 in a pattern which concentrates the electromagnetic energy in a zone in which the plasma generator tube 230 is positioned. A tuning rod 240 can be vertically positioned to tune the electromagnetic waves to provide optimum plasma generation. The gas plasma is then fed to the gas distributor 212 and its Y-or T-distribution section 241. The horizontal distributors have angular outlet ports positioned and with angular displacement as described with respect to the preferred embodiment of FIG. 5, FIG. 6 and FIG. 7. The plasma is directed through a change of direction of 90° at least twice before it is discharged into the sterilizing chamber. This prevents direct impingement of hot nascent plasma onto the articles being sterilized, greatly reducing the oxidation of sensitive packaging materials by the plasma.

Figure 15:
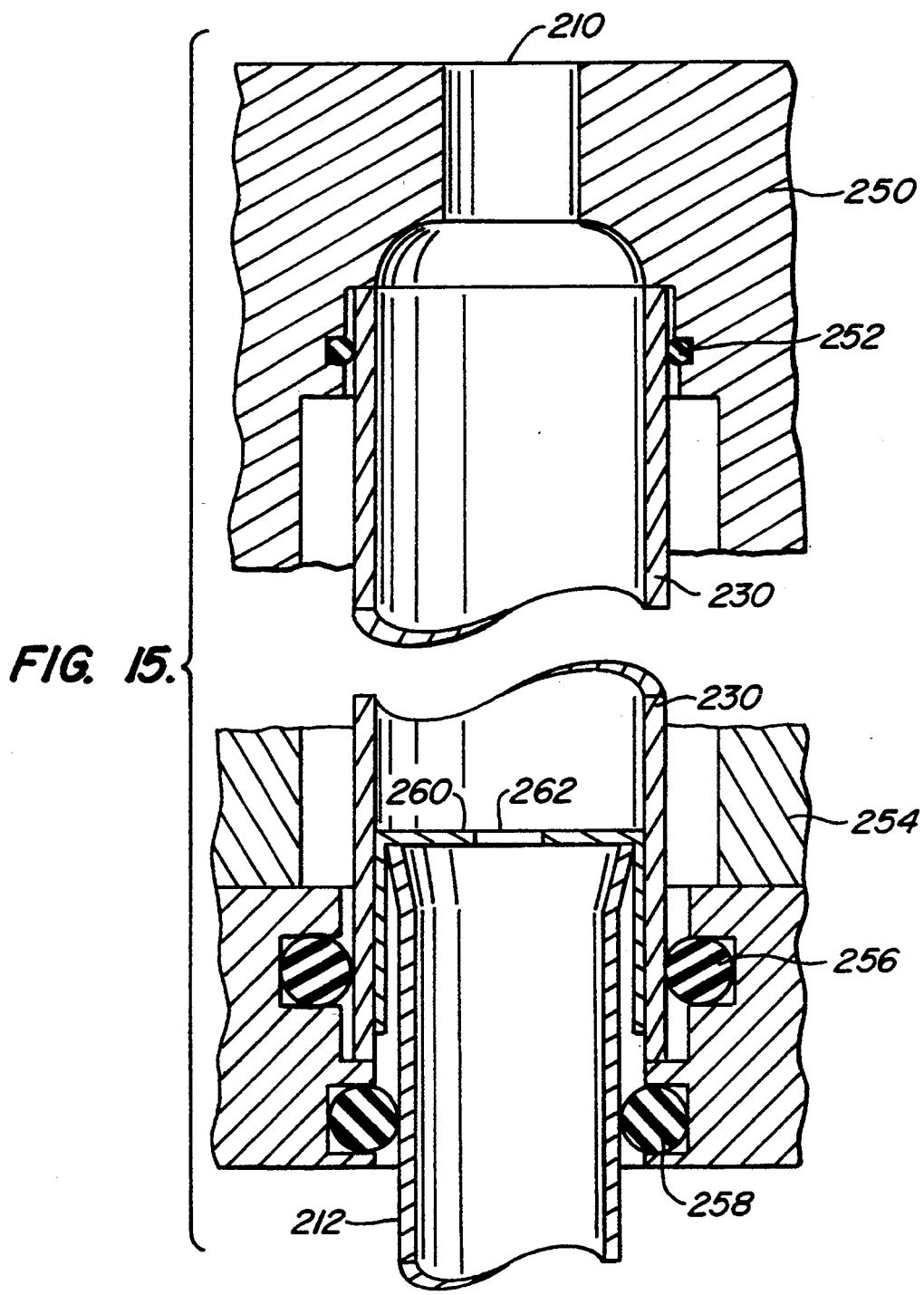
FIG. 15 is a partial cross-sectional view of the plasma generator tube and assembly of the embodiment of FIG. 13.

FIG. 15 is a fragmentary, cross-sectional view of the plasma generating tube of the plasma generator shown in FIG. 14, showing details of the tube construction and its connection with the gas distributor tube. The tube 230 is held in a sealed engagement with the heat radiating cap 250 by O-ring 252 or a similar seal. The lower distal end of the tube is also held in a sealed engagement with the lower heat radiator sleeve 254 by an O-ring 256. The proximal end of the distribution tube 212 extends into the distal end of tube 230 and is held in a sealed relationship with the lower heat radiator sleeve by an O-ring 258. Cap 260 is positioned on the proximal end of plasma distribution tube 212 and has a preselected restrictive opening 262 of further reduced cross-sectional area. As described with respect to the embodiment shown in FIG. 9, the restriction is a critical aspect of the embodiment, creating a pressure difference between the low pressure plasma generating zone and the vacuum pressure in the distribution tube and sterilizing chamber.

The diameter of the restrictive opening 262 is selected to maintain a back pressure of from 0.3 to 10 torr and preferably from 1 to 5 torr in the plasma generating zone with a vacuum chamber pressure in the range of from 0.3 to 2 torr. This pressure provides optimum energy consumption and plasma generation and is a major factor for the production of a high yield of plasma at a minimum temperature and with the minimum power requirement achieved with this device. For most operating parameters, the restriction 262 can have a diameter of from 4.82 to 8.00 mm and preferably from 6.28 to 6.54 mm.

The plasma sterilizer embodiments suitable for use in the process of this invention have been presented with three plasma generating units. The number of generating units is not critical, being selected to provide a good plasma distribution in the particular sterilizing chamber used. Any desired number of plasma generators can be used with each sterilizing chamber and are intended to be included within the scope of this invention. It is also readily apparent that any number of gas plasma tubes can be positioned to interact with the electromagnetic field generated from a single magnetron with this waveguide configuration, and that other waveguide configurations can be used to achieve this effect. The preferred plasma generating tubes and plasma distributing tubes are made of quartz. However, any other materials with the necessary physical, chemical and electrical properties for plasma generation in an electromagnetic field and for transport of plasma can be used and are intended to be included.

We claim:

1. A method for plasma sterilization comprising exposing an article in a sterilizing chamber under a preselected temperature to a non-explosive mixture of 1% to 20% (v/v) oxygen and a gas plasma until the article is sterilized, said gas plasma being generated by a plasma generation means from a mixture of 1% to 20% (v/v) hydrogen and an inert gas at a pressure of from 0.1 to 10 torr, and said non-explosive mixture of oxygen being introduced downstream of said gas plasma generation means.

2. A method of claim I wherein the oxygen concentration is from 1% to 10% (v/v) oxygen.

3. A method of claim 2 wherein the hydrogen concentration is from 1% to 5% (v/v).

4. A method of claim 1 wherein the pressure in the sterilizing chamber is from 1 to 10 torr.

5. A method of claim 1 wherein the article is enclosed in a package including a porous organic layer, and the preselected temperature is up to 60° C.

6. A method of claim 6 wherein the porous organic layer contains cellulose or an organic polymer.

7. A method of claim 1 wherein the article is metal and the preselected temperature is up to 80° C.

8. A method for sterilization of an article comprising the steps of:

generating a plasma stream in a plasma generating chamber by subjecting a gas mixture stream to a plasma inducing means;

combining an oxygen or oxygen containing stream with said plasma stream downstream from the plasma inducing means; and exposing the article to the combined plasma stream and oxygen or oxygen containing stream in a sterilization chamber to effect sterilization.

9. A method for sterilization of an article as in claim 8, wherein said gas mixture stream includes a non-explosive mixture of oxygen.

10. A method of claim 8 wherein the article is enclosed in a package including a porous organic layer, and the preselected temperature is up to 60° C.

11. A method of claim 10 wherein the porous organic layer contains cellulose or an organic polymer.

* * * * *

UNITED STATES PATENT AND TRADEMARK OFFICE
CERTIFICATE OF CORRECTION

PATENT NO. : 5,376,332
DATED : December 27, 1994
INVENTOR(S) : Martens et al.

It is certified that error appears in the above-indentified patent and that said Letters Patent is hereby corrected as shown below:

In Column 11, Line 16 in Claim 2:
Replace "2. A method of claim I wherein the oxygen concen-" with --2. A method of claim 1 wherein the oxygen concen- --

In Column 12, Line 1 in Claim 6:
Replace "6. A method of claim 6 wherein the porous organic" with --6. A method of claim 5 wherein the porous organic--

Signed and Sealed this

Eighteenth Day of April, 1995

Attest:

BRUCE LEHMAN

Attesting Officer

Commissioner of Patents and Trademarks